United States Patent [19]

Young

[11] Patent Number: 5,674,188
[45] Date of Patent: Oct. 7, 1997

[54] CONSTRUCTION FOR ORTHOPEDIC HINGES REQUIRING CONDYLAR OR OTHER JOINT PADS

[76] Inventor: David Ernest Young, Bowler's Piece, 16 Couching Street, Watlington, Oxfordshire, United Kingdom, OX9 5QQ

[21] Appl. No.: 521,842

[22] Filed: Aug. 31, 1995

[51] Int. Cl.⁶ .................................................. A61F 5/00
[52] U.S. Cl. ........................................ 602/26; 602/16
[58] Field of Search .............................. 602/5, 16, 23, 602/26

[56] References Cited

U.S. PATENT DOCUMENTS

| | | |
|---|---|---|
| 4,249,524 | 2/1981 | Anderson . |
| 4,337,764 | 7/1982 | Lerman . |
| 4,370,977 | 2/1983 | Mauldin et al. . |
| 4,489,718 | 12/1984 | Martin . |
| 4,520,802 | 6/1985 | Mercer et al. . |
| 4,620,532 | 11/1986 | Houswerth . |
| 4,697,583 | 10/1987 | Mason et al. . |
| 4,732,143 | 3/1988 | Kausek et al. . |
| 4,803,975 | 2/1989 | Meyers ........................... 602/26 |
| 4,854,308 | 8/1989 | Drillio ......................... 602/26 X |
| 4,881,299 | 11/1989 | Young et al. . |
| 4,915,098 | 4/1990 | Young et al. . |
| 4,928,670 | 5/1990 | DeLorenzo ...................... 602/26 |
| 4,940,045 | 7/1990 | Cromartie ..................... 602/26 X |
| 4,991,571 | 2/1991 | Kausik ......................... 602/26 X |
| 5,000,170 | 3/1991 | Young et al. . |
| 5,038,765 | 8/1991 | Young et al. . |
| 5,039,247 | 8/1991 | Young et al. . |
| 5,042,464 | 8/1991 | Skwor et al. ................... 602/26 X |
| 5,131,385 | 7/1992 | Kuehnegger et al. ............ 602/26 X |
| 5,168,865 | 12/1992 | Radcliffe et al. .............. 602/26 X |
| 5,316,547 | 5/1994 | Gildersleeve .................... 602/26 |
| 5,336,161 | 8/1994 | Lengyel ........................... 602/26 |
| 5,527,268 | 6/1996 | Gildersleeve et al. ............ 602/26 |

FOREIGN PATENT DOCUMENTS

| | | |
|---|---|---|
| 1299455 | 4/1992 | Canada . |
| 0327286 | 4/1992 | European Pat. Off. . |
| 499208 | 2/1939 | United Kingdom . |
| 2163352 | 2/1986 | United Kingdom . |
| 2182714 | 5/1987 | United Kingdom . |
| 2208065 | 2/1989 | United Kingdom . |

*Primary Examiner*—Linda C. Dvorak
*Attorney, Agent, or Firm*—Tilton, Fallon & Lungmus

[57] ABSTRACT

An improved condylar platen an pad construction for use with most types of hinges used in orthopedica and orthotic appliances integrates, by moulding, a hinge back plate with a joint pad platen and shimming means. The platen has a flexible margin portion disposed about an extension molded peripheral to the enclosed hinge back plate. The flexible margin may be contoured for conformability to a joint. The extension creates a recess between the flexible margin and the hinge back plate. A joint pad is air and foam filled and a central portion of it fits within the recess of the platen and a peripheral portion locates on the flexible margin. The condylar pad is covered overall by a bonnet. The improved condylar platen construction eliminates drag between a platen and hinge arms and accelerates and eases manufacture by reducing and combining parts. The instant pad is more versatile and functionally effective than prior art pads.

23 Claims, 5 Drawing Sheets

CONSTRUCTION FOR ORTHOPEDIC HINGES REQUIRING CONDYLAR OR OTHER JOINT PADS

FIELD OF THE INVENTION

The invention relates to hinges which are used in orthopedic and orthotic practice to make braces and other appliances for use at human joints.

BACKGROUND OF THE INVENTION AND THE PRIOR ART

There are many hinge designs used in orthopedic and orthotic braces and splints.

In a first widely used type at the knee, hip and elbow, there are two hinge arms jointed at and flexing about a single pivot. This type is generally referred to by those skilled in the art as the uni-axial, uni-pivotal or monocentric type.

The present author was the the first inventor of a single flexion axis hip described in GB 2 163 352. Other single pivot hinges described in the patent literature include U.S. Pat. No. 4,370,977 to Mauldin and Driver, U.S. Pat. No. 4,489,718 to Martin and U.S. Pat. No. 4,620,532 to Housewerth.

In a second type, perhaps even more widely used, particularly at the knee, there are two hinge arms, each having its own pivot and also each having a set of gear teeth about the periphery of the part which extends between the pivots. The arms are so sized and arranged that the gear teeth mesh between the pivot points, thereby integrating the arm movements. Thus if one arm moves, the other must move as well. This type is generally referred to by those skilled in the art as the geared bi-axial, geared duocentric or geared polycentric type. The latter term is perhaps the most widely recognized.

Some examples of geared polycentric two pivot hinges include U.S. Pat. No. 4,337,764 to Lerman, U.S. Pat. No. 4,697,583 to Mason et al. and U.S. Pat. No. 4,732,143 to Kausek.

A third type also has two hinge arms, each having its own pivot but in this design there are gear teeth. Thus, the arm movements are not integrated and each arm can always move independently without affecting the other. This type of hinge is generally referred to by those skilled in the art as the true bi-axial, true bi-pivotal or simply just bi-pivotal type.

The present author has been the first inventor of a number of orthopedic hinges with two independent pivots. Some examples include patents GB 2 182 714 and U.S. and EPO counterparts U.S. Pat. Nos. 4,915,098 and 327,286, respectively; GB 2 208 065 and U.S. counterpart U.S. Pat. Nos. 4,881,299; 5,000,170 and Canadian counterpart 1,299,455; U.S. Pat. Nos. 5,038,765 and 5,039,247.

Other patents disclosing hinges with two independently pivoting arms includes U.S. Pat. No. 4,249,524 to Anderson, U.S. Pat. No. 4,520,802 to Mercer and Aaserude and U.K. 499 208 to Griffiths (not orthopedic).

Both bi-pivotal hinges and geared polycentric hinges are, in mechanical terms, three bar linkages. However, the integration of the hinge arms in the geared polycentric type causes the loss of one degree of freedom.

There is a small number other types of hinge used in orthopedic and orthotic appliances based, for instance, on sliding pivots and four bar mechanisms but these are not widely employed in commercially available devices.

The present invention is applicable to most uni-axial, geared polycentric and true bi-pivotal hinges as well as to some of the less widely used types.

Of concern to those who make and design braces is the total number of parts to be handled during manufacture, since the greater the number and complexity of parts, the greater the skill needed and the more time taken in assembly. This ultimately reflects in increased cost to the end user.

In recent years, a great deal of attention has been paid by those skilled in the art to the design of functional knee braces which are intended to provide stability for unstable knees. Current opinion favors designs in which hinges are disposed in close approximation to the knee, have minimal thickness profiles and are provided with joint pads called condylar pads.

Several types of condylar pads have been used and the earliest examples were simple applique pads with no special platen structure. These pads were generally formed plastics, usually but not always a closed cell type, such as expanded polyethylene or expanded polyvinyl alcohol, attached to the inside of each hinge back plate using adhesives.

The present author has designed braces employing this type of condylar pad including two products called Masterbrace™ and Masterbrace™II. These are made by Protectair Limited of Abingdon U.K. and are currently sold by Johnson & Johnson Professional of Bracknell, U.K. and Raynham, Mass., U.S.A. in a number of countries including the U.K. and the U.S.A.

Where platens have been employed they have usually been a shaped die-cut, vacuum formed or molded entity used as mount for a condylar pad. The aim in shaping a platen is to present the pad in a more anatomical manner to a curved surface about a condyle of a joint. If a continuous condylar pad is used with such a platen, extending over the entire surface, the assembly will have the advantage of being more comfortable. This is because the pad will be compressed more or less evenly over a large contact area. This contrasts with the flat applique pad which depends upon compression forces delivered via the brace straps to force a flat entity into conformity with a curved body surface.

In 1984 the present author designed a molded dished platen which used a continuous condylar pad. This was and still is employed as an optional "knee cage" in two products called "Rehabilitative Knee Brace" and "Adjustabrace™", both made and sold by the commercial companies referenced above. This entity is mounted upon and spaced apart from the inner surface of a hinge back plate on one or more hexagonal-bodied spacer bolt parts. Each has a female threaded recess in the head end and a male thread on the shank. These have the disadvantage in a normal knee that even deploying one such spaced tends to space the platen off the back of the hinge, towards to knee joint, rather more than is desirable. Thus, nowadays, their use is mainly confined to special applications involving deformed joints.

From inspection of products in the market place and from manufacturers' literature, the author has found two basic constructions for condylar pad platens; no specific platen constructions were discovered in the patent literature scrutinized although an exhaustive search was not possible.

A non-exclusive example of the first type is used on a functional knee brace product called "Legend™", made by Don Joy, Inc. of Carlsbad, Calif., U.S.A., where a shaped, molded, flexible condylar pad platen is made from plastics and is secured against an inner hinge cover, also made from plastics. Both elements are secured together against a hinge back plate with rivet securing means which also provide pivot means. The pivot rivet securing means pass through hinge arms and a hinge front plate to which they are clenched to complete the basic hinge assembly.

A non-exclusive example of the second type is used on another functional knee brace product called "Edge™", made by Innovation Sports of Irvine, Calif., U.S.A., where a metal hinge back plate is secured over part of a small, shaped, condylar pad platen, molded in a rubber material, by screw means which engage with pivot boss means provided by and arising from a hinge front plate.

These constructions suffer from a common disadvantage due to the condylar platen being anchored against the back of the hinge plate or mechanism. This is that the platen and condylar pad assembly, being so closely coupled to the back of the hinge, can impinge during use, on the inner surfaces of the hinge arms, causing drag. Only if the platen and pad were to be made so small as to be of doubtful support value would the risk of impingement in this type of design be completely avoided.

Additionally, in the riveted type, especially where, as in the example quoted, the rivets must pass through more than one layer of plastic, the recognized phenomenon of creep is aggravated by cyclic flexing of the platen during use. These factors will work against the rivets and are bound to cause loosening and general deterioration of the brace hinge over time.

Apart from applique and continuous platen molded pads, another obvious but not very satisfactory solution has been adopted by several manufacturers in recent years. This has been to adapt the donut-shaped air filled pads from ear defenders as condylar pads. Those skilled in the art will be aware that joint condyles present hard eminences with limited soft tissue covering and this is one reason why condylar pads are favored. However, when a brace with a simple donut pad is applied to a joint, the flexible platen is bent outwards and the empty center of the donut allows the hard or minimally lined platen and hinge back plate to be pressed against the condylar eminence causing discomfort and sometimes, pain.

Furthermore, tests on several manufacturer's braces carried out early in 1995, at Leighton Hospital, Crewe, U.K., led the author to observe that dependent braces, such as knee braces, fitted with air filled condylar pads suffer "peristaltic" effects. As the knee flexes and extends, such pads are locally and differentially compressed, leading to the transfer of air between the proximal and distal portions of the pad on a cyclic basis. When the air in such a pad is compressed above a bony eminence, the pad effectively pushes the brace distally, worsening a common problem encountered with knee braces known as "ride-down". This term is used by those skilled in the art to describe slippage of a brace down the leg. The human leg, in any case, has a natural, more or less conical, proximal to distal profile and it will be appreciated that a relatively small distal displacement of a brace will result in loss of contact and further, more profound, slippage.

Donut-shaped air filled condylar pads are less effective than applique or continuous pads because not only do they worsen ride-down and fail to provide useful pad thickness over the center of the hinge back plate, they also become completely ineffective if punctured.

SUMMARY OF THE INVENTION

The present invention provides a condylar platen construct and condylar pad for improved construction of virtually any design of orthopedic hinge which can accommodate two hinge arms, pivotally mounted on one or more pivots, a hinge back plate and pivotal securing means for securing the hinge arms to the back plate and which in addition uses pivot washers or shimming means (or which would benefit therefrom) between the hinge arms and hinge back plate. The instant construction is employed when it is desired to provide a condylar or other joint pad for a joint such as the knee or elbow.

According to a first aspect of the invention, a condylar platen construct is molded in suitable plastics over an insert hinge back plate, preferably made in metals or alternatively in hard structural composites and having one or more through holes adapted to receive pivot securing means. The condylar platen construct additionally provides integral planar shimming means over one entire face of the hinge back plate which, by virtue of selecting materials having very low friction characteristics, are effectively self-lubricating for the anticipated life of the hinge.

According to a second aspect of the invention, the condylar pad platen molding has an extension, peripheral to the incorporated hinge back plate and directed towards the joint.

According to a third aspect of the invention, the condylar pad platen of the construct has a substantial flexible margin, disposed about the peripheral extension, which is optimally asymmetrical and which may, additionally, be contoured in a manner generally similar to the part of the body over which it is to be positioned.

Provision of the extension peripheral to the hinge back plate creates a recess between this and the flexible margin. The extension spaces the flexible margin away from the hinge arms and prevents impingement, thereon, during use. In addition, the extension isolates the flexing portion of the condylar pad platen from the overmolded hinge back plate.

According to a fourth aspect of the invention, a compressible condylar pad is provided which has a central portion, so sized and shaped that it forms a downstand, which engages with the recess in the condylar pad platen. It also has a peripheral portion, which is similar in plan view to and slightly larger in area than the flexible margin of the condylar pad platen upon which it is located.

According to a fifth aspect of the invention, the compressible condylar pad has a first, flexible and preferably sealed enclosing stucture, having a partial filling of air and a second, filling element comprising cushions made in resilient foamed plastics.

It is, therefore, the principal object of this invention to provide a novel condylar pad platen, integrated with a hinge back plate and shimming means into one component, for an orthopedic hinge having at least one pivot.

It is another important object of this invention to provide a novel compressible condylar pad, for use with the instant condylar pad platen, which has a downstanding central portion and a peripheral portion, both portions being filled with a combination of air and resilient foamed plastics.

It is another important aspect of this invention to provide resilient foamed plastic cushions for the instant condylar pad where the cushion provided for the central portion and that provided for the peripheral portion of the pad may be similar or they may differ and in either case may be made of more than one type of resilient foamed plastics. By these means, a condylar pad, according to the instant invention, may be made more or less compressible according to therapeutic need.

Other objects and advantages will become clear as the present invention is described in greater detail, by way of example only, with reference to the accompanying drawings.

BRIEF DESCRIPTION OF THE DRAWINGS

In general, a convention has been adopted of describing the position of structural elements in drawings in relation to their anatomical disposition, using such terms as "anterior" and "posterior" to describe fore and rear with respect to a human body upon which a device, incorporating the present invention, would be used.

DETAILED DESCRIPTION OF THE PREFERRED EMBODIMENT

With general reference to FIGS. 1–12, a condylar platen construct and a compressible condylar pad for an orthopedic hinge, according to a most preferred embodiment of the present invention, have the general designations 10 and 12, respectively. It is to be understood that 10, 12 will be used together as a combined entity and generally but not always, in a paired configuration, with one such entity being disposed as part of a hinge on one side of a joint and another such entity being disposed as part of a hinge on the other side of the same joint.

Figure 1:
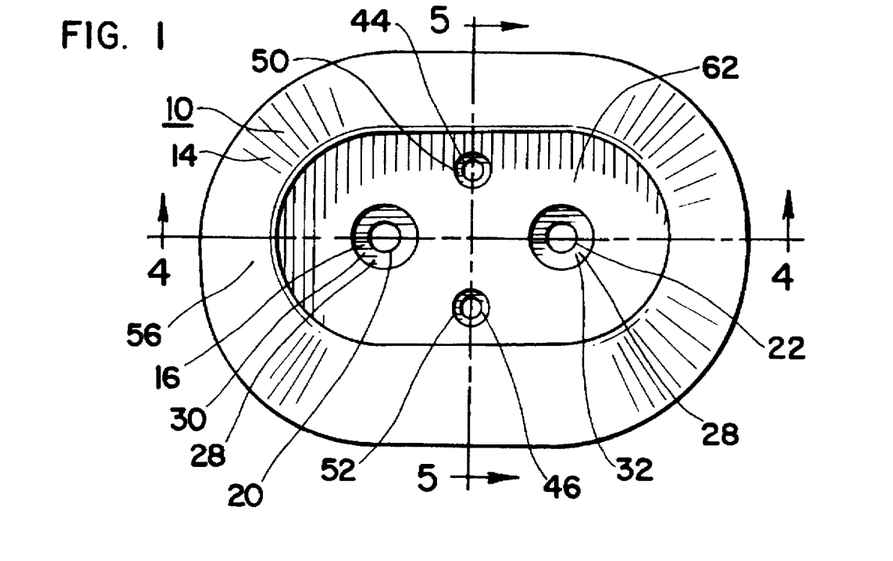
FIG. 1 is an inner, joint side, plan view of a condylar platen construct comprising a condylar pad platen, a hinge back plate and a shim, according to the present invention, for use with an orthopedic or orthotic hinge.

Condylar platen construct 10 comprises a novel condylar pad platen 14 and a substantially flat hinge back plate 16 preferably made in metals such as aluminum, stainless steel or titanium but alternatively made in hard structural composite materials. Hinge back plate 16 is incorporated into condylar platen construct 10 by inserting it into an injection mold and molding it substantially overall. Condylar pad platen 14 is made of suitable plastics, such as a flexible grade of nylon 6.

The overmolding is effected in such a manner that hinge back plate 16 is provided, with a molded integral planar shim 18, which by virtue of the low friction characteristics of the materials selected, is effectively self-lubricating for the anticipated life of the hinge.

Figure 12:
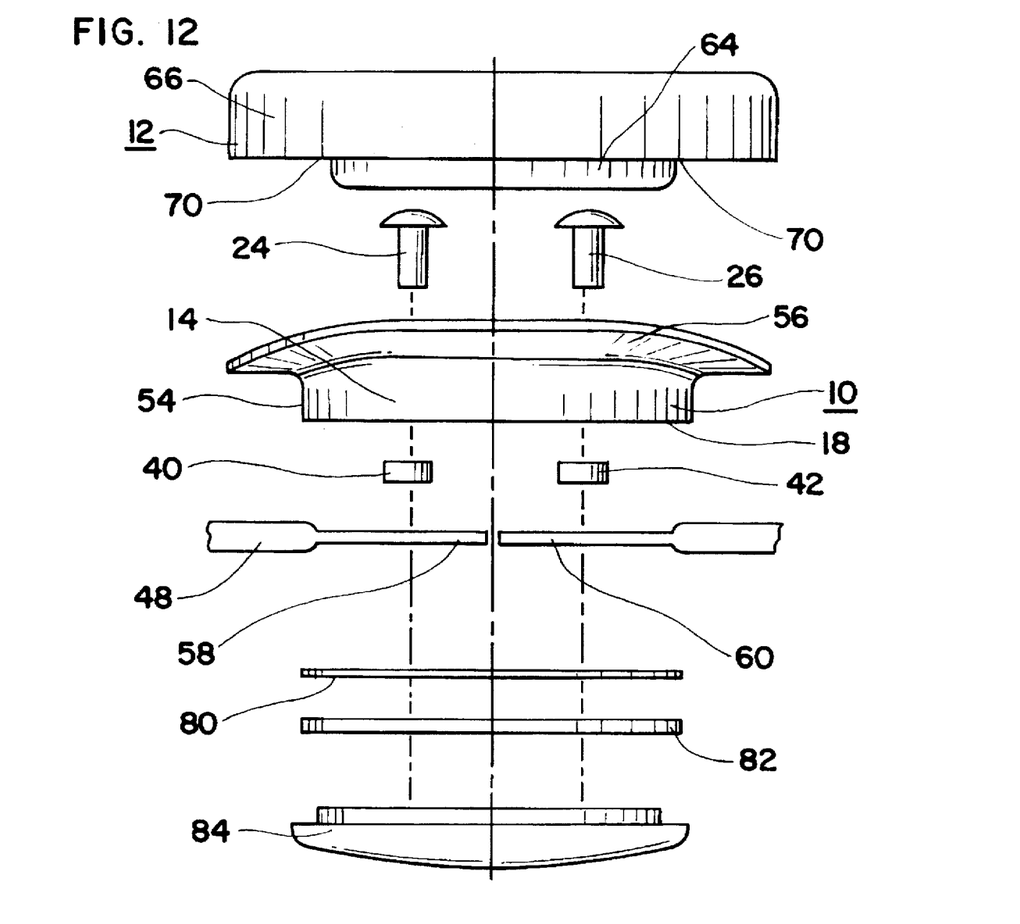
FIG. 12 is an exploded front view of the hinge of FIG. 11, showing the relationship of the condylar platen construct and compressible condylar pad, to other salient structures thereof.

Hinge back plate 16 is adapted by the provision of through pivot holes 20 and 22 for the receival of pivot rivet securing means 24 and 26 (seen only in FIG. 12). On its first, inner or platen face 28 condylar platen construct 10 has hinge back plate 16 exposed in areas 30 and 32 surrounding pivot holes 20 and 22.

Figure 2:
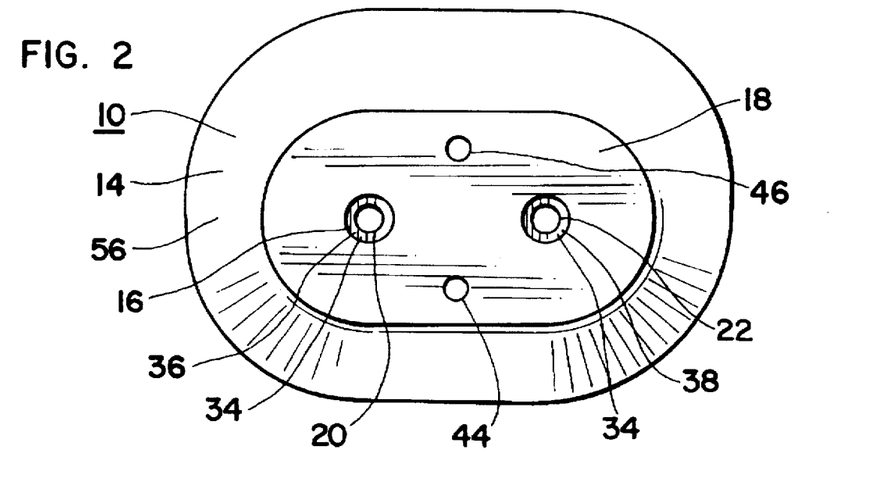
FIG. 2 is an outer, hinge side, underplan view of the condylar platen construct of FIG. 1.
Figure 3:
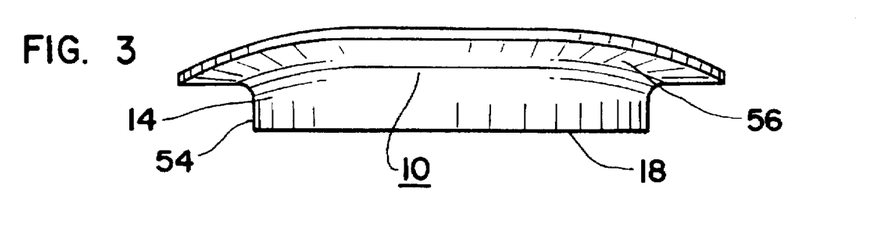
FIG. 3 is a posterior side view of the condylar platen construct of FIG. 1.
Figure 4:
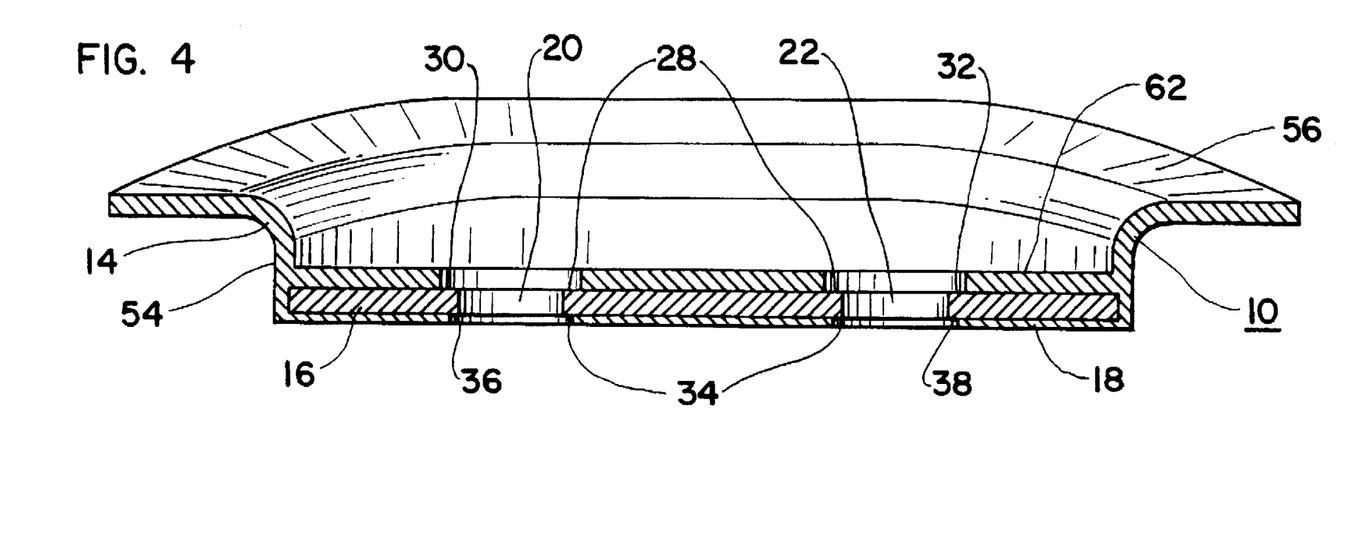
FIG. 4 is a sectional posterior side view, at enlarged scale, of the condylar platen construct along a line a–a$^1$, in FIG. 1, showing the hinge plate incorporated therein.

In this embodiment, other areas of hinge back plate 16 are exposed on second, outer or hinge face 34 of condylar platen construct 10 at 36 and 38. These are provided to allow hinge bushings 40 and 42 (also seen only in FIG. 12) to be secured against hinge back plate 16, allowing metal to metal contact. This is preferable engineering practice to allowing bushings 40 and 42 to be compressed against the plastic of integral planar shim 18, which extends substantially over second, outer or hinge face 34.

Hinge back plate 16 is also adapted by the provision of through clearance holes 44 and 46, for the receival of screws (not illustrated) concerned in the assembly of an orthopedic hinge 48. The heads of these screws locate in recesses formed between the plastic first, inner or platen face 28 of condylar platen construct 10 and exposed metal areas 50 and 52 of hinge back plate 16.

Figure 5:
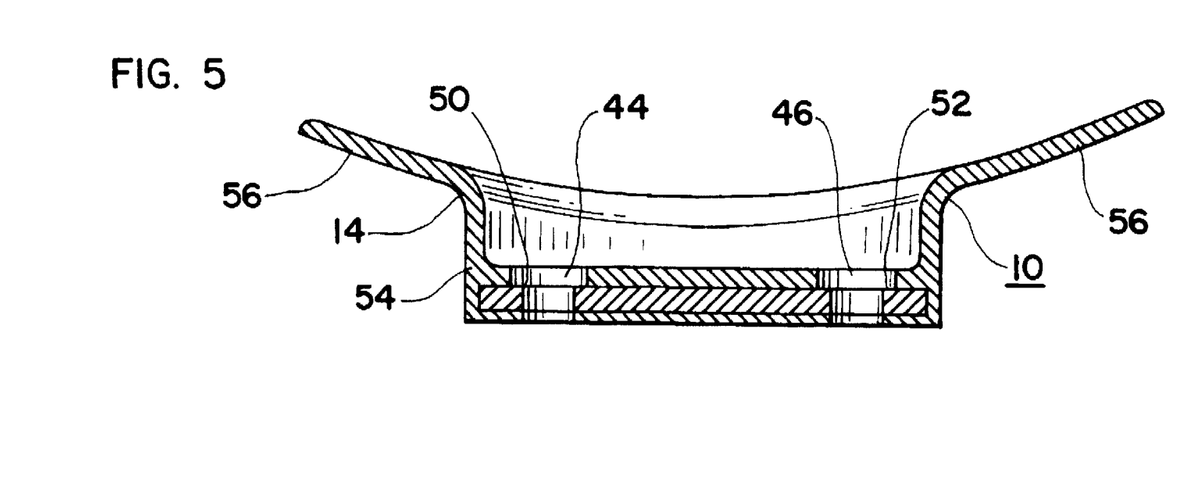
FIG. 5 is a sectional distal end view, at enlarged scale, of the condylar platen construct along a line b–b$^1$, in FIG. 1, showing preferred asymmetry of the flexible margin of the condylar pad platen molding.

As may be seen by brief reference to FIGS. 2 and 5, there are no exposed areas of hinge plate 16 corresponding to 50 and 52 on second, outer or hinge face 34 because there are no structures operating against either 16 or integral planner shim 18 at those positions.

That part of the condylar pad platen molding 14 immediately peripheral to hinge back plate 16 is formed into an extension 54 towards the joint. The purpose of extension 54 is to ensure that when a flexible margin 56 of condylar pad platen 14 and a compressible condylar pad 12 located thereupon are compressed against a joint, flexible margin 56 may conform thereto but is effectively prevented from impinging upon hinge arms 58 and 60 of an orthopedic hinge 48 into which it is incorporated. By this novel means, drag on hinge arms 58 and 60 is avoided.

Flexible margin 56 of condylar pad platen 14 extends about extension 54 of hinge back plate 16 to provide a substantial platform for compressible condylar pad 12. In this embodiment, which is for a knee hinge, flexible margin 56 is asymmetrical, resembling a modified ellipse or modified rectangle and being larger anteriorly than posteriorly. Flexible margin 56 has a guttered or open-ended trough profile.

The provision of extension 54 creates a shallow recess 62, similar in shape to and slightly larger in area than, hinge back plate 16.

Figure 6:
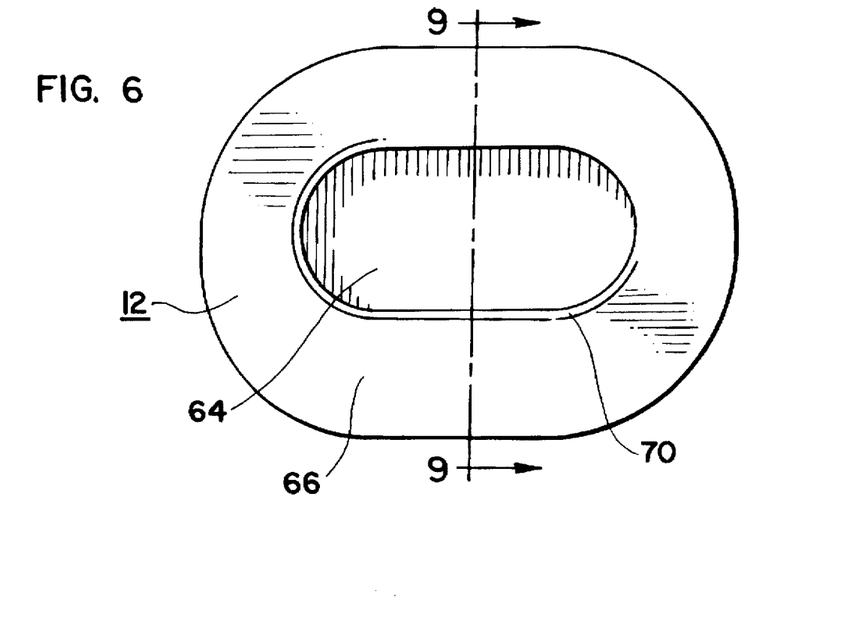
FIG. 6 is an inner, joint side, plan view of a compressible condylar pad, according to the present invention, for use with the condylar platen construct of FIG. 1.
Figure 7:
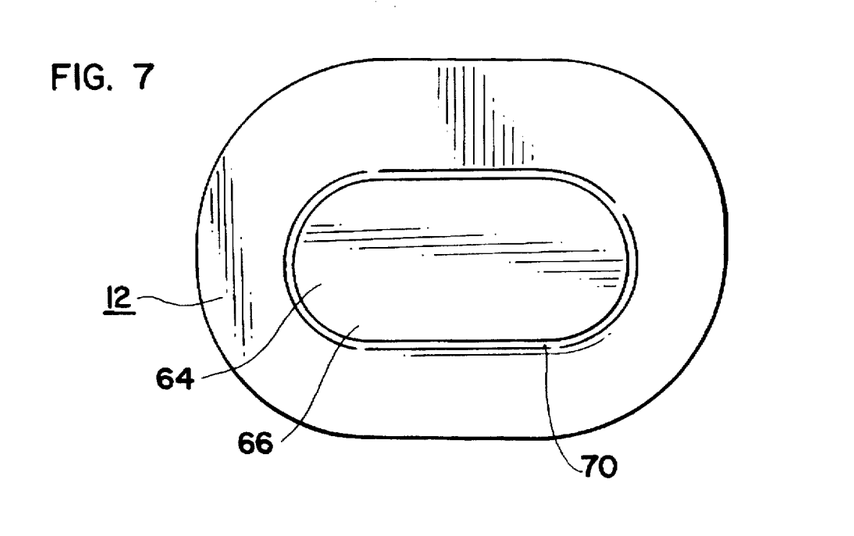
FIG. 7 is an outer, platen side, underplan view of the compressible condylar pad of FIG. 6.
Figure 8:
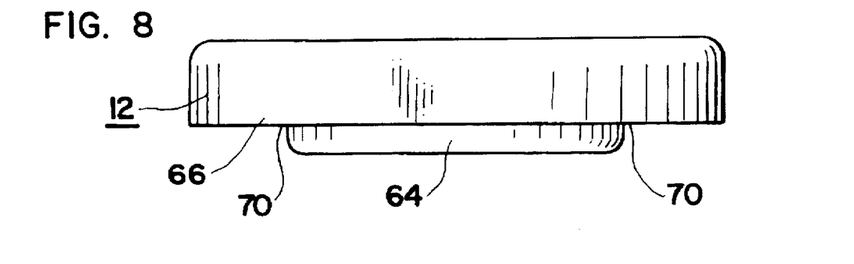
FIG. 8 is a side view of the compressible condylar pad of FIG. 6.

A novel compressible condylar pad 12 has a central portion 64, so sized and shaped that it forms a downstand which substantially engages with recess 62 in condylar pad platen 14. Compressible condylar pad 12 also has a peripheral portion 66, which is similar in plan view to and slightly larger than, flexible margin 56 of condylar pad platen 14, upon which it rests.

Figure 9:
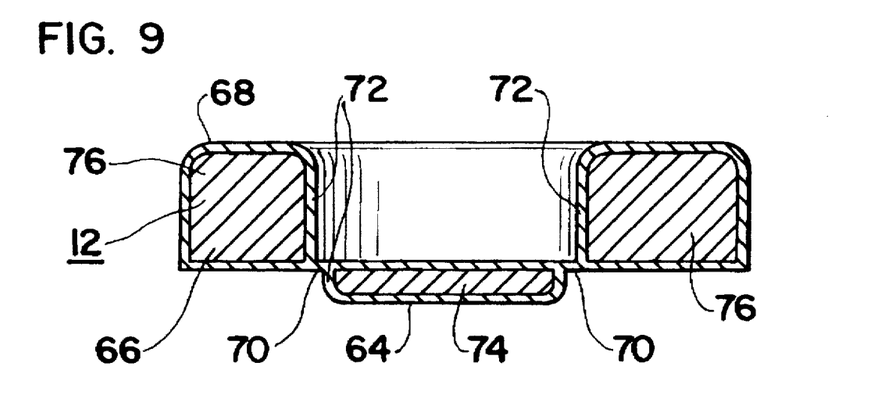
FIG. 9 is a sectional distal end view of the compressible condylar pad along a line c–c$^1$, in FIG. 6, showing cushions incorporated therein and preferred anterior asymmetry.

As seen in FIG. 9, compressible condylar pad 12 has a first element in the form of a flexible enclosing structure 68, which is formed, preferably, from a plurality of layers of textiles reinforced film plastics, sealed by high frequency welding in a suitable vacuum forming and die-cutting tool. This produces a narrow linear sealing zone 70 disposed between central portion 64 and peripheral portion 66.

Flexible enclosing structure 68 has a partial filling of air indicated at 72 but additional and novel elements are in the form of cushions 74 and 76 provided within central portion 64 and peripheral portion 66, respectively. Cushions 74 and 76 are preferably made in resilient foamed plastics, which may be of open cell or closed cell type or a combination of both types. If only closed cell foam is used it preferably has an uncompressed volume about 20% less than the total volume of flexible enclosing structure 68. It is not necessary to form compressible condylar pad 12 to the gutter profile of flexible margin 56 of condylar pad platen 14 since the inherent flexibility and resilience of the materials from which 12 is made is sufficient to accommodate such contouring as is likely to be required.

Tests have shown that an important advantage of compressible condylar pads using resilient foamed plastics cushions in a flexible enclosing structure is that they are much less prone to peristaltic effects. Thus, during cyclic flexion and extension of the limb segments about the joint, any tendency of an appliance, so provided, to ride down a limb is much reduced in comparison to that encountered when prior art condylar pads, filled with air alone, are used.

Another advantage of the instant compressible condylar pads with combined resilient foamed plastics cushions and air filling is that they retain function if trapped air is lost. Indeed, if a combination of open and closed cell foams is used, it becomes possible to offer the end user the option to puncture one or both of portions 64 and 66 of compressible condylar pad 12 for a firmer but still functional fit. Furthermore, it is possible to engineer a series of resilient foamed plastics cushions for a number of different purposes, such as providing different levels of compressibility at different stages of treatment. This may be accomplished by, for instance, laminating together layers of resilient foamed plastics of different density or type, such as a combination of open and closed cell types. Subject only to the characteristics of the foamed materials selected, the cushions may be die-cut or may, alternatively, be compression molded. Of course, the cushion employed in central portion 64 of compressible condylar pad 12 need not have the same composition of characteristics as that employed in peripheral portion 66.

Figure 10:
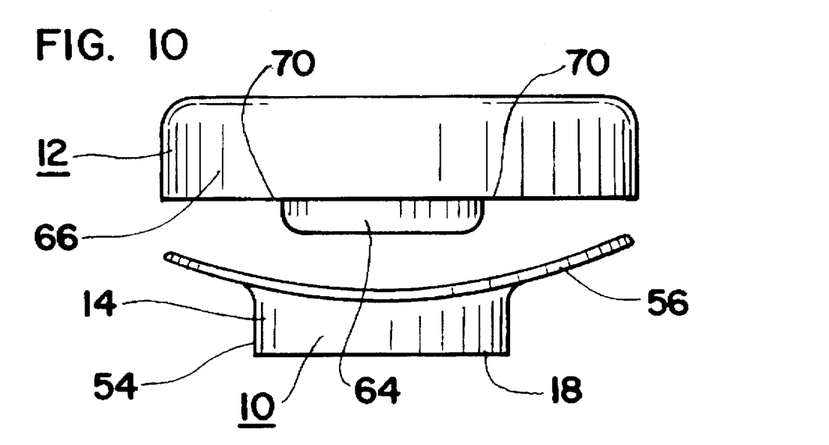
FIG. 10 is an anterior front view of an orthopedic hinge, having two pivots and incorporating a condylar platen construct comprising a condylar pad platen, hinge back plate and shim, together with a compressible condylar pad and bonnet, according to the present invention.
Figure 11:
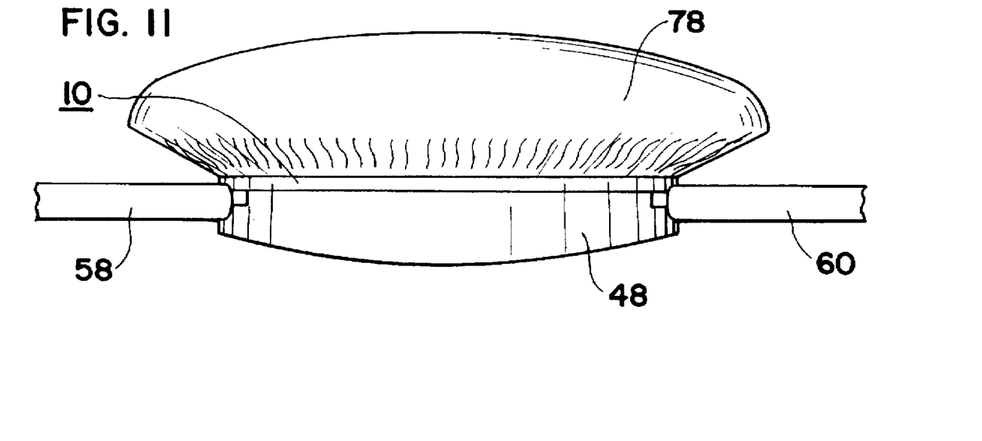
FIG. 11 is an anterior front view of an orthopedic hinge, having two pivots and incorporating a condylar platen construct comprising a condylar pad platen, hinge back plate and shim, together with a compressible condylar pad and bonnet, according to the present invention.

In FIG. 10, compressible condylar pad 12 is shown, unflexed, adjacent to condylar platen construct 10 in approximate functional relationship. When 12 is actually fitted to 10 it will, of course, deform somewhat as it takes up the anterior to posterior curvature of flexible margin 56. As is suggested by FIG. 10, central portion 64 of compressible condylar pad 12 is somewhat smaller in area than recess 62 (not annotated in FIG. 10) of condylar pad platen 14. Thus, peripheral portion 66 of compressible condylar pad 12 and not sealing zone 70 overlies extension 54, ensuring that a condition of an unpadded edge lying against a bony eminence cannot occur. In any case, it is to be borne in mind that the dimension of 54 will only be so great as is necessary to ensure that flexible margin 56 will not impinge on the arms of the hinge being designed. Although it is dependent upon the configuration of the hinge arms in any given hinge, the dimension of 54 can generally be kept to 5 to 6 mm and the overall profile of orthopedic hinges using the condylar platen construct of the present invention may be kept very slim indeed.

Peripheral portion 66 of compressible condylar pad 12 is retained on flexible margin 56 of condylar pad platen 14 by a bonnet 78 made of suitable fabrics such as a polyester material and which is self-retaining by virtue of having elastic edging means. Bonnet 78 provides an overall cover for compressible condylar pad 12 and condylar pad platen 14.

For security and ease of manufacture, the underside of central portion 64 of compressible condylar pad 12 may be secured within recess 62 using a combination of self-adhesive hook and loop materials (not illustrated).

In some circumstances, it may be preferred to use the instant condylar pad platen with a compressible condylar pad other than that immediately hereinbefore described in respect of the first and most preferred embodiment.

In a second and also preferred embodiment, there is no flexible enclosing structure. A cushion is compression molded in closed cell resilient foamed plastics and is analogous to compressible condylar pad 12 of the first embodiment. It has a central portion which occupies recess 62 and a peripheral portion which locates on flexible margin 58 with a compressed zone between the two portions which is analogous to sealing zone 70. It has similar dimensions to compressible condylar pad 12.

In another preferred embodiment, two separate cushions are deployed. A first cushion occupies recess 62 and a second cushion extends over the entire inner aspect of condylar pad platen 14, including the first cushion. Overall dimensions are similar to those of compressible condylar pad 12.

In another preferred embodiment, also involving two cushions, a first cushion occupies recess 62 and extends through a second, ring-shaped cushion which extends over and is located upon flexible margin 56. Once again, overall dimensions are similar to those of compressible condylar pad 12.

To conclude this brief review of the versatility of the instant compressible condylar pads, in a variant of the first and most preferred embodiment, central portion 64 of compressible condylar pad 12 additionally extends partially or fully upwards through peripheral portion 66. Flexible enclosing structure 68 and sealing zone 70 are retained.

Bonnet 78 is used in all of these embodiments of a compressible condylar pad and condylar platen construct 10 is unaltered in all cases.

As disclosed, areas of condylar platen construct 10 about pivot holes 20 and 22 for accepting pivot securing means, are relieved, exposing first, inner or platen face 28 of hinge back plate 16 at 30 and 32. Pivotal securing means may be in the form of rivet means or screw means, acting in cooperation with, for instance, bushing means. If rivet means are employed, as in the preferred embodiment, it is desirable that exposed areas 30 and 32 about through holes 20 and 22 are large enough to provide access for the anvil part of a riveting press during assembly.

It is to be understood that, if the hinge has two pivots, there will preferably be provided one relieved area for each pivot rivet or screw, as described, rather than one large area of exposed metal. This is in order that the strength and integrity of condylar platen construct 10 is not compromised.

FIG. 12 shows the principal parts of an orthopedic hinge employing the instant invention. Consideration of this figure will indicate that, in this hinge, though not all hinges, the element of a front shim 80 is important and the element of a front hinge plate 82 is essential. Front hinge cover 84 is desirable for cosmetic reasons but in a functional knee brace is also constitutes a guard against impingement of metal parts upon the brace wearer and other participants in contact sports.

A very important advantage of instant condylar platen construct 10 is that it is extremely strong and completely eliminates the tendency of prior art, separate condylar platens, to work against pivot securing means, particularly pivot rivet means, which inevitably loosen. This is achieved first by isolating flexible margin 56 of condylar pad platen 14 from the pivot securing means by means of extension 54 and second by the provision of exposed metal areas 30 and 32 about pivot rivet securing means 24 and 26, allowing metal to metal contact. This eliminates the inevitable creep effects that obtain where metal securing means are clenched against conventional plastics.

Further advantages of instant condylar pad platen derive from contouring flexible margin 56 which confers better limb conformability and also by positioning it inboard of hinge back plate 16 which eliminates the risk of impingement of hinge arms and consequent platen drag seen in prior art constructions.

In summary, in contra-distinction to prior art condylar platens and pads, the instant combination of condylar platen construct 10 and compressible condylar pad 12 offers improved conformability to the limb, improved progressive padding over the entire platen (and therefore the hinge) and longer hinge life at unimpaired performance levels with smoother operation. By combining at least three prior art components into condylar platen construct 10, the instant invention is much easier to use in building up a hinge, saving time and attendant labor costs. Finally, the instant invention provides the opportunity to design condylar pads for use with the instant condylar pad platen 14 which are more varied, versatile and therapeutically appropriate than those of the prior art.

While the present invention has been described in respect of particular embodiments, further modifications may readily be made by those skilled in the art. It is intended that the claims should cover any such modifications falling within the spirit and scope of the invention.

I claim:

1. An assembly of a condylar platen construct and a condylar pad for an orthopaedic hinge; said construct comprising a hinge back plate having first and second faces on opposite sides thereof and having one or more through holes for receiving hinge arm pivot means; a platen for a condylar pad; said platen being injection molded of flexible plastic and having portions extending around and over both of said faces of said back plate to incorporate said back plate within said platen; said platen having an integral flexible peripheral extension projecting in a direction away from said second face of said back plate to provide a flexible contoured margin and, in combination with the portion of said platen extending over said second face of said back plate, defining a recess for receiving at least a portion of a condylar pad; said portion of said platen extending over said first face providing integral planar shimming means for an orthopaedic hinge when said construct is in use; and a compressible condylar pad engaging said peripheral extension and having at least a portion thereof received in said recess.

2. The assembly of claim 1 wherein said hinge back plate is made of hard structural composite materials.

3. The assembly of claim 1 wherein exposed areas of said hinge back plate are provided around one or more of said through holes on said first face.

4. The assembly of claim 1 wherein exposed areas of said hinge back plate are provided around one or more of said through holes on said second face.

5. The assembly of claim 1 wherein said injection molded plastic of said platen has low friction properties and said integral planar shimming means formed therein are thereby effectively self-lubricating.

6. The assembly of claim 1 wherein said flexible margin is asymmetrical with respect to hinge back plate.

7. The assembly of claims 1 or 6 wherein said flexible margin has an open-ended trough profile.

8. The assembly of claims 1 or 6 wherein said flexible margin is contoured with respect to the plane of said hinge back plate.

9. The assembly of claim 1 wherein said compressible condylar pad includes a first element in the form of a flexible enclosing structure formed of plastic and containing air; said first element extending below the general plane of said compressible condylar pad so as to form a downstand so sized and shaped as to substantially engage said recess in said platen; said first element also including a second peripheral portion extending above the general plane of said compressible condylar pad so sized and shaped as to locate generally upon said flexible margin portion of said platen; and a sealing zone disposed between said first central portion and said second peripheral portion of said first element; said compressible condylar pad also including a second element in the form of first and second cushions made of resilient foamed plastic; said first cushion being located within said central portion and said second cushion being located within said peripheral portion of said first element.

10. The assembly of claim 9 wherein said flexible enclosing structure is sealed against the ingress and egress of air.

11. The assembly of claim 9 wherein said enclosing structure has provision for ingress and egress of air.

12. The assembly of claim 9 wherein each of said first and second cushions is made from closed cell resilient foamed plastic.

13. The assembly of claim 9 wherein each of said first and second cushions is made from a combination of more than one type of resilient foamed plastic.

14. The assembly of claim 9 wherein said first and second cushions are made by diecutting.

15. The assembly of claim 9 wherein said first and second cushions are made by compression molding.

16. The assembly of claim 9 wherein said first central portion additionally extends upwardly through said peripheral portion.

17. The assembly of claim 1 wherein a first cushion element is provided for said recess in said platen and a second cushion element extends over the entire plan area of said flexible margin an said first cushion element.

18. The assembly of claim 1 wherein a first cushion element is provided for said recess in said platen which extends through a second cushion element having the form of a ring and which extends over said flexible margin of said platen.

19. The assembly of claims 17 or 18 wherein each of said first and second cushion elements is made from closed cell foamed plastic.

20. The assembly of claims 17 or 18 wherein each of first and second cushion elements is made from the same resilient foamed plastic.

21. The assembly of claims 17 or 18 wherein said first and second cushion elements are made from different resilient foamed plastic.

22. The assembly of claims 9, 17 or 18 wherein securing means are provided for securing said compressible condylar pad to said platen; said securing means comprising a fabric bonnet having an elasticized edge.

23. The assembly of claim 1 wherein said compressible condylar pad includes a first central portion extending below the general plane of said compressible condylar pad so as to form a downstand so sized and shaped as to substantially engage said recess in said platen, and a second peripheral portion extending above the general plane of said compressible condylar pad, so sized and shaped as to locate generally upon said flexible margin portion of said platen; said compressible condylar pad being formed of resilient foamed plastic.

* * * * *